(12) United States Patent
Howard

(10) Patent No.: US 11,998,455 B2
(45) Date of Patent: *Jun. 4, 2024

(54) SYSTEMS AND METHODS FOR EXPANDABLE CORPECTOMY SPACER IMPLANTATION

(71) Applicant: GLOBUS MEDICAL, INC., Audubon, PA (US)

(72) Inventor: George Howard, Green Lane, PA (US)

(73) Assignee: Globus Medical, Inc., Audubon, PA (US)

( * ) Notice: Subject to any disclaimer, the term of this patent is extended or adjusted under 35 U.S.C. 154(b) by 0 days.

This patent is subject to a terminal disclaimer.

(21) Appl. No.: 18/151,541

(22) Filed: Jan. 9, 2023

(65) Prior Publication Data
US 2023/0255787 A1 Aug. 17, 2023

Related U.S. Application Data

(63) Continuation of application No. 17/094,177, filed on Nov. 10, 2020, now Pat. No. 11,596,526, which is a continuation-in-part of application No. 16/371,419, filed on Apr. 1, 2019, now Pat. No. 10,881,528, which is a continuation of application No. 15/836,362, filed on Dec. 8, 2017, now Pat. No. 10,278,834, which is a continuation-in-part of application No. 15/264,974, filed on Sep. 14, 2016, now Pat. No. 10,278,833.

(51) Int. Cl.
*A61F 2/44* (2006.01)

(52) U.S. Cl.
CPC ............... *A61F 2/4465* (2013.01); *A61F 2/44* (2013.01); *A61F 2/446* (2013.01); *A61F 2002/448* (2013.01); *A61F 2002/4495* (2013.01)

(58) Field of Classification Search
CPC .......... A61F 2/44; A61F 2/442; A61F 2/4455; A61F 2/4465; A61F 2002/443; A61F 2002/4435
See application file for complete search history.

(56) References Cited

U.S. PATENT DOCUMENTS

| | | | |
|---|---|---|---|
| 4,349,921 | A | 9/1982 | Kuntz |
| 4,599,086 | A | 7/1986 | Doty |
| 4,863,476 | A | 9/1989 | Shepperd |
| 4,863,477 | A | 9/1989 | Monson |
| 5,123,926 | A | 6/1992 | Pisharodi |

(Continued)

FOREIGN PATENT DOCUMENTS

| AU | 2008224951 A1 | * | 9/2009 | ............ A61B 17/70 |
|---|---|---|---|---|
| CA | 2088066 A1 | | 1/1992 | |

(Continued)

*Primary Examiner* — Eric S Gibson

(57) ABSTRACT

An implant assembly including an expandable vertebral body replacement implant. Two outer cores disposed on opposing ends of an inner are configured to move away from each other when the inner core is actuated. The implant assembly may include removable endplate configured to engage vertebral bodies as interbody spacer or through a corpectomy. The implant may include a locking mechanism to prevent collapse or movement the implant assembly after implantation. The locking mechanism may be automatically engage after removal of an inserter instrument from the implant assembly.

18 Claims, 24 Drawing Sheets

(56) References Cited

U.S. PATENT DOCUMENTS

| | | |
|---|---|---|
| 5,192,327 A | 3/1993 | Brantigan |
| 5,290,312 A | 3/1994 | Kojimoto et al. |
| 5,306,310 A | 4/1994 | Siebels |
| 5,375,823 A | 12/1994 | Navas |
| 5,390,683 A | 2/1995 | Pisharodi |
| 5,522,899 A | 6/1996 | Michelson |
| 5,534,030 A | 7/1996 | Navarro et al. |
| 5,554,191 A | 9/1996 | Lahille et al. |
| 5,571,190 A | 11/1996 | Ulrich et al. |
| 5,571,192 A | 11/1996 | Schonhoffer |
| 5,645,596 A | 7/1997 | Kim |
| 5,653,763 A | 8/1997 | Errico et al. |
| 5,665,122 A | 9/1997 | Kambin |
| 5,676,701 A | 10/1997 | Yuan et al. |
| 5,702,451 A | 12/1997 | Biedermann et al. |
| 5,702,455 A * | 12/1997 | Saggar ............... A61F 2/44 623/17.15 |
| 5,897,556 A | 4/1999 | Drewry et al. |
| 6,039,761 A | 3/2000 | Li et al. |
| 6,045,579 A | 4/2000 | Hochschuler et al. |
| 6,080,193 A | 6/2000 | Hochschuler et al. |
| 6,086,613 A | 7/2000 | Camino |
| 6,099,531 A | 8/2000 | Bonutti |
| 6,126,689 A | 10/2000 | Brett |
| 6,159,211 A | 12/2000 | Boriani et al. |
| 6,176,882 B1 | 1/2001 | Biedermann et al. |
| 6,258,125 B1 | 7/2001 | Paul et al. |
| 6,558,423 B1 | 5/2003 | Michelson |
| 6,562,074 B2 | 5/2003 | Gerbec et al. |
| 6,576,016 B1 | 6/2003 | Hochschuler et al. |
| 6,554,863 B2 | 8/2003 | Paul et al. |
| 6,641,614 B1 | 11/2003 | Wagner et al. |
| 6,648,917 B2 | 11/2003 | Gerbec et al. |
| 6,666,891 B2 | 12/2003 | Boehm, Jr. et al. |
| 6,692,495 B1 | 2/2004 | Zacouto |
| 6,706,070 B1 | 3/2004 | Wagner et al. |
| 6,752,832 B2 | 6/2004 | Ulrich |
| 6,758,862 B2 | 7/2004 | Berry et al. |
| 6,776,798 B2 | 8/2004 | Camino et al. |
| 6,814,756 B1 | 11/2004 | Michelson |
| 6,830,589 B2 | 12/2004 | Erickson |
| 6,849,093 B2 | 2/2005 | Michelson |
| 6,852,129 B2 | 2/2005 | Gerbec et al. |
| 6,863,673 B2 | 3/2005 | Gerbec et al. |
| 6,881,228 B2 | 4/2005 | Zdeblick et al. |
| 6,899,734 B2 | 5/2005 | Castro et al. |
| 7,018,415 B1 | 3/2006 | McKay |
| 7,070,598 B2 | 7/2006 | Lim et al. |
| 7,204,853 B2 | 4/2007 | Gordon |
| 7,217,291 B2 | 5/2007 | Zucherman et al. |
| 7,282,063 B2 | 10/2007 | Cohen et al. |
| 7,309,358 B2 | 12/2007 | Berry et al. |
| 7,316,714 B2 | 1/2008 | Gordon |
| 7,473,276 B2 | 1/2009 | Aebi et al. |
| 7,473,277 B2 * | 1/2009 | Boyer, II ............ A61F 2/44 623/17.11 |
| 7,544,208 B1 | 6/2009 | Mueller et al. |
| 7,547,325 B2 | 6/2009 | Biedermann et al. |
| 7,575,601 B2 * | 8/2009 | Dickson ............... A61F 2/44 623/17.15 |
| 7,621,953 B2 | 11/2009 | Braddock, Jr. et al. |
| 7,641,693 B2 | 1/2010 | Gutlin et al. |
| 7,682,396 B2 | 3/2010 | Beaurain et al. |
| 7,749,270 B2 | 7/2010 | Peterman |
| 7,753,958 B2 | 7/2010 | Gordon |
| 7,771,473 B2 | 8/2010 | Thramann |
| 7,780,732 B2 | 8/2010 | Abernathie |
| 7,799,081 B2 | 9/2010 | McKinley |
| 7,815,683 B2 | 10/2010 | Melkent et al. |
| 7,837,734 B2 | 11/2010 | Zucherman et al. |
| 7,875,078 B2 | 1/2011 | Wysocki et al. |
| 7,887,594 B2 | 2/2011 | Berry et al. |
| 7,901,409 B2 | 3/2011 | Canaveral et al. |
| 7,909,869 B2 | 3/2011 | Gordon |
| 7,951,199 B2 | 5/2011 | Miller |
| 7,985,256 B2 | 7/2011 | Grotz et al. |
| 8,062,375 B2 | 11/2011 | Glerum |
| 8,070,813 B2 | 12/2011 | Grotz et al. |
| 8,123,810 B2 | 2/2012 | Gordon |
| 8,137,405 B2 | 3/2012 | Kostuik et al. |
| 8,182,537 B2 * | 5/2012 | Refai ............... A61F 2/44 623/17.16 |
| 8,192,495 B2 | 6/2012 | Simpson et al. |
| 8,197,546 B2 * | 6/2012 | Doubler ............ A61F 2/44 606/279 |
| 8,231,681 B2 * | 7/2012 | Castleman ......... A61F 2/44 623/17.16 |
| 8,273,126 B2 * | 9/2012 | Lindner ............ A61F 2/4611 623/17.11 |
| 8,282,683 B2 * | 10/2012 | McLaughlin ...... A61F 2/4455 623/17.11 |
| 8,292,963 B2 * | 10/2012 | Miller ............... A61F 2/44 606/252 |
| 8,303,663 B2 | 11/2012 | Jimenez et al. |
| 8,377,140 B2 | 2/2013 | DeFalco et al. |
| 8,394,129 B2 | 3/2013 | Lopez et al. |
| 8,394,143 B2 | 3/2013 | Grotz et al. |
| 8,435,296 B2 | 5/2013 | Kadaba et al. |
| 8,454,695 B2 | 6/2013 | Grotz et al. |
| 8,647,386 B2 | 2/2014 | Gordon |
| 8,696,751 B2 | 4/2014 | Ashley et al. |
| 8,771,360 B2 | 7/2014 | Jimenez et al. |
| 8,894,710 B2 | 11/2014 | Simpson et al. |
| 8,900,308 B2 * | 12/2014 | Biedermann ...... A61F 2/4465 623/17.11 |
| 8,932,355 B2 | 1/2015 | Grotz et al. |
| 8,940,049 B1 | 1/2015 | JImenez et al. |
| 8,956,413 B2 | 2/2015 | Ashley et al. |
| 8,992,620 B2 | 3/2015 | Ashley et al. |
| 9,028,550 B2 | 5/2015 | Shulock et al. |
| 9,301,850 B2 * | 4/2016 | McLaughlin ...... A61F 2/446 |
| 9,358,125 B2 | 6/2016 | JImenez et al. |
| 9,474,621 B2 * | 10/2016 | McLaughlin ...... A61F 2/4455 |
| 9,532,883 B2 | 1/2017 | McLuen et al. |
| 9,622,878 B2 | 4/2017 | Grotz |
| 9,687,357 B2 * | 6/2017 | Bannigan .......... A61F 2/4455 |
| 10,758,365 B2 * | 9/2020 | Cummins ........... A61F 2/30771 |
| 11,596,526 B2 * | 3/2023 | Howard ............. A61F 2/4465 |
| 2002/0045945 A1 | 4/2002 | Liu |
| 2002/0068976 A1 | 6/2002 | Jackson |
| 2002/0068977 A1 | 6/2002 | Jackson |
| 2003/0176926 A1 | 9/2003 | Boehm et al. |
| 2003/0191531 A1 | 10/2003 | Berry et al. |
| 2004/0030387 A1 | 2/2004 | Landry et al. |
| 2004/0049270 A1 | 3/2004 | Gewirtz |
| 2004/0049271 A1 | 3/2004 | Biedermann |
| 2004/0054412 A1 | 3/2004 | Gerbec et al. |
| 2004/0087947 A1 | 5/2004 | Lim et al. |
| 2004/0153065 A1 | 8/2004 | Lim |
| 2005/0021041 A1 | 1/2005 | Michelson |
| 2005/0021145 A1 | 1/2005 | de Villiers et al. |
| 2005/0033432 A1 | 2/2005 | Gordon |
| 2005/0080422 A1 | 4/2005 | Otte et al. |
| 2005/0090898 A1 * | 4/2005 | Berry ............... A61F 2/44 623/17.11 |
| 2005/0113916 A1 | 5/2005 | Branch |
| 2005/0149188 A1 | 7/2005 | Cook |
| 2005/0171541 A1 | 8/2005 | Boehm |
| 2005/0251258 A1 | 11/2005 | Jackson |
| 2005/0273171 A1 | 12/2005 | Gordon |
| 2005/0273174 A1 | 12/2005 | Gordon |
| 2005/0278026 A1 | 12/2005 | Gordon |
| 2005/0283244 A1 | 12/2005 | Gordon |
| 2005/0283245 A1 | 12/2005 | Gordon |
| 2006/0004453 A1 | 1/2006 | Bartish, Jr. et al. |
| 2006/0015184 A1 | 1/2006 | Winterbottom et al. |
| 2006/0058878 A1 | 3/2006 | Michelson |
| 2006/0084986 A1 | 4/2006 | Grinberg et al. |
| 2006/0122701 A1 | 6/2006 | Kister |
| 2006/0129244 A1 | 6/2006 | Ensign |
| 2006/0142859 A1 | 6/2006 | Mcluen |
| 2006/0149385 A1 | 7/2006 | Mckay |
| 2006/0195192 A1 | 8/2006 | Gordon et al. |

(56) References Cited

U.S. PATENT DOCUMENTS

| | | |
|---|---|---|
| 2006/0229729 A1 | 10/2006 | Gordon |
| 2006/0241770 A1 | 10/2006 | Rhoda et al. |
| 2006/0253201 A1 | 11/2006 | Mcluen |
| 2007/0043442 A1 | 2/2007 | Abernathie |
| 2007/0050030 A1 | 3/2007 | Kim |
| 2007/0050032 A1 | 3/2007 | Gittings et al. |
| 2007/0055377 A1 | 3/2007 | Hanson et al. |
| 2007/0191951 A1 | 8/2007 | Branch |
| 2007/0255415 A1 | 11/2007 | Edie et al. |
| 2007/0255421 A1* | 11/2007 | Dickson ............... A61F 2/44 623/17.15 |
| 2007/0270963 A1 | 11/2007 | Melkent et al. |
| 2007/0270968 A1 | 11/2007 | Baynham |
| 2008/0021559 A1 | 1/2008 | Thramann |
| 2008/0065222 A1 | 3/2008 | Hamada |
| 2008/0114467 A1 | 5/2008 | Capote et al. |
| 2008/0140207 A1 | 6/2008 | Olmos et al. |
| 2008/0147194 A1 | 6/2008 | Grotz et al. |
| 2008/0161933 A1 | 7/2008 | Grotz et al. |
| 2008/0167657 A1 | 7/2008 | Greenhalgh |
| 2008/0183204 A1 | 7/2008 | Greenhalgh et al. |
| 2008/0221694 A1 | 9/2008 | Warnick et al. |
| 2008/0275455 A1 | 11/2008 | Berry et al. |
| 2008/0281346 A1 | 11/2008 | Greenhalgh et al. |
| 2008/0288073 A1 | 11/2008 | Renganath et al. |
| 2008/0300598 A1 | 12/2008 | Barreiro et al. |
| 2008/0306488 A1 | 12/2008 | Altarac et al. |
| 2008/0319487 A1 | 12/2008 | Fielding et al. |
| 2008/0319549 A1 | 12/2008 | Greenhalgh et al. |
| 2009/0024217 A1 | 1/2009 | Levy et al. |
| 2009/0036985 A1 | 2/2009 | Whiting |
| 2009/0062833 A1 | 3/2009 | Song |
| 2009/0076616 A1 | 3/2009 | Duggal et al. |
| 2009/0112325 A1* | 4/2009 | Refai ............... A61F 2/44 623/17.15 |
| 2009/0125062 A1 | 5/2009 | Arnin |
| 2009/0149956 A1 | 6/2009 | Greenhalgh et al. |
| 2009/0149959 A1 | 6/2009 | Conner et al. |
| 2009/0187248 A1 | 7/2009 | Dewey et al. |
| 2009/0204218 A1 | 8/2009 | Richelsoph |
| 2009/0222100 A1 | 9/2009 | Cipoletti et al. |
| 2009/0240334 A1 | 9/2009 | Richelsoph |
| 2009/0270989 A1 | 10/2009 | Conner et al. |
| 2009/0281628 A1 | 11/2009 | Oglaza et al. |
| 2009/0292361 A1 | 11/2009 | Lopez |
| 2009/0299478 A1 | 12/2009 | Carls et al. |
| 2009/0312763 A1 | 12/2009 | McCormack |
| 2010/0049324 A1 | 2/2010 | Valdevit |
| 2010/0070041 A1 | 3/2010 | Peterman |
| 2010/0082109 A1 | 4/2010 | Greenhalgh et al. |
| 2010/0145455 A1 | 6/2010 | Simpson et al. |
| 2010/0179657 A1 | 7/2010 | Greenhalgh et al. |
| 2010/0211176 A1 | 8/2010 | Greenhalgh |
| 2010/0222816 A1 | 9/2010 | Gabelberger et al. |
| 2010/0274357 A1* | 10/2010 | Miller ............... A61F 2/4611 623/17.11 |
| 2010/0286783 A1 | 11/2010 | Lechmann et al. |
| 2011/0035011 A1 | 2/2011 | Cain |
| 2011/0093074 A1 | 4/2011 | Glerum et al. |
| 2011/0106258 A1 | 5/2011 | Blackwell et al. |
| 2011/0160861 A1 | 6/2011 | Jimenez et al. |
| 2011/0172774 A1 | 7/2011 | Varela |
| 2011/0251691 A1* | 10/2011 | McLaughlin ......... A61F 2/4611 623/17.16 |
| 2011/0276142 A1 | 11/2011 | Niemiec et al. |
| 2011/0301713 A1 | 12/2011 | Theofilos |
| 2011/0319997 A1 | 12/2011 | Glerum et al. |
| 2012/0035729 A1 | 2/2012 | Glerum et al. |
| 2012/0059470 A1 | 3/2012 | Weiman |
| 2012/0059472 A1 | 3/2012 | Weiman |
| 2012/0109308 A1 | 5/2012 | Lechmann et al. |
| 2012/0130496 A1 | 5/2012 | Duffield et al. |
| 2012/0165945 A1 | 6/2012 | Hansell et al. |
| 2012/0179255 A1 | 7/2012 | Defalco et al. |
| 2012/0185049 A1 | 7/2012 | Varela |
| 2012/0209386 A1 | 8/2012 | Triplett et al. |
| 2012/0215313 A1 | 8/2012 | Saidha et al. |
| 2012/0226357 A1 | 9/2012 | Varela |
| 2012/0265303 A1* | 10/2012 | Refai ............... A61F 2/44 623/17.11 |
| 2012/0265309 A1 | 10/2012 | Glerum et al. |
| 2012/0277861 A1 | 11/2012 | Steele et al. |
| 2012/0277870 A1 | 11/2012 | Wolters et al. |
| 2012/0323329 A1 | 12/2012 | Jimenez et al. |
| 2012/0330426 A1 | 12/2012 | McLaughlin et al. |
| 2013/0023993 A1 | 1/2013 | Weiman |
| 2013/0023994 A1 | 1/2013 | Glerum |
| 2013/0158663 A1 | 6/2013 | Miller et al. |
| 2013/0158669 A1 | 6/2013 | Sungarian et al. |
| 2013/0197647 A1 | 8/2013 | Wolters et al. |
| 2013/0211526 A1 | 8/2013 | Alheidt et al. |
| 2013/0274883 A1 | 10/2013 | McLuen et al. |
| 2013/0330059 A1 | 12/2013 | Matsumoto et al. |
| 2013/0331943 A1* | 12/2013 | Arnold ............... A61F 2/4455 623/17.15 |
| 2014/0067071 A1 | 3/2014 | Weiman et al. |
| 2014/0088714 A1 | 3/2014 | Miller et al. |
| 2014/0107787 A1 | 4/2014 | Stinchfield et al. |
| 2014/0142706 A1* | 5/2014 | Hansell ............... A61F 2/44 623/17.16 |
| 2014/0156006 A1* | 6/2014 | Bannigan ............... A61F 2/44 623/17.15 |
| 2014/0163683 A1 | 6/2014 | Seifert et al. |
| 2014/0207235 A1 | 7/2014 | Drapeau |
| 2015/0066145 A1 | 3/2015 | Rogers et al. |
| 2015/0088258 A1 | 3/2015 | Jimenez et al. |
| 2015/0134064 A1 | 5/2015 | Grotz et al. |
| 2015/0216676 A1 | 8/2015 | Shulock et al. |
| 2015/0289988 A1 | 10/2015 | Ashley et al. |
| 2015/0374508 A1 | 12/2015 | Sandul |
| 2016/0100955 A1* | 4/2016 | Stinchfield ............ A61F 2/4465 623/17.15 |
| 2016/0166396 A1 | 6/2016 | McClintock |
| 2016/0324654 A1 | 11/2016 | Loebl et al. |
| 2017/0100258 A1 | 4/2017 | Jimenez et al. |
| 2017/0119543 A1 | 5/2017 | Dietzel et al. |
| 2018/0318107 A1* | 11/2018 | Cummins ............ A61F 2/30771 |
| 2021/0059835 A1* | 3/2021 | Howard ............... A61F 2/30744 |
| 2021/0330471 A1* | 10/2021 | Dewey ............... A61F 2/4425 |
| 2022/0023066 A1* | 1/2022 | Howard ............... A61F 2/4611 |
| 2022/0241085 A1* | 8/2022 | Berry ............... A61F 2/4425 |
| 2023/0255787 A1* | 8/2023 | Howard ............... A61F 2/4465 623/17.16 |

FOREIGN PATENT DOCUMENTS

| | | | |
|---|---|---|---|
| CN | 1483389 A | 3/2004 | |
| DE | 4012622 C1 | 7/1991 | |
| DE | 4327054 C1 | 4/1995 | |
| EP | 0576379 B1 | 6/1993 | |
| EP | 0610837 B1 | 7/1994 | |
| EP | 2421477 B1 * | 2/2014 | ............... A61F 2/44 |
| EP | 3111896 A1 | 1/2017 | |
| FR | 2794968 A1 | 12/2000 | |
| JP | 2000-513263 A | 10/2000 | |
| JP | 2001526083 | 12/2001 | |
| JP | 2001526083 A | 12/2001 | |
| JP | 2011502004 A | 1/2011 | |
| JP | 2013-523406 A | 6/2013 | |
| JP | 2013-176696 A | 9/2013 | |
| KR | 200290058 Y1 | 9/2002 | |
| SU | 1424826 A1 | 9/1988 | |
| WO | 9201428 A1 | 2/1992 | |
| WO | 9525485 A1 | 9/1995 | |
| WO | 9932055 A1 | 7/1999 | |
| WO | 1999042062 A1 | 8/1999 | |
| WO | 1999066867 A1 | 12/1999 | |
| WO | 01/70139 A2 | 9/2001 | |
| WO | 0170139 A2 | 9/2001 | |
| WO | 2002045625 A1 | 6/2002 | |
| WO | 2004019829 A1 | 3/2004 | |
| WO | 2004069033 A2 | 8/2004 | |
| WO | 2005070346 A1 | 8/2005 | |

(56) References Cited

FOREIGN PATENT DOCUMENTS

| WO | 2006045094 A2 | 4/2006 | | |
|---|---|---|---|---|
| WO | 2006047587 A2 | 5/2006 | | |
| WO | 2006113080 A2 | 10/2006 | | |
| WO | 2008044057 A1 | 4/2008 | | |
| WO | 2008134515 A1 | 11/2008 | | |
| WO | 2009114381 A1 | 9/2009 | | |
| WO | 2010103344 A1 | 9/2010 | | |
| WO | WO-2010124008 A2 * | 10/2010 | ............... | A61F 2/44 |
| WO | 2012031267 A1 | 3/2012 | | |
| WO | 2015009793 A1 | 1/2015 | | |

* cited by examiner

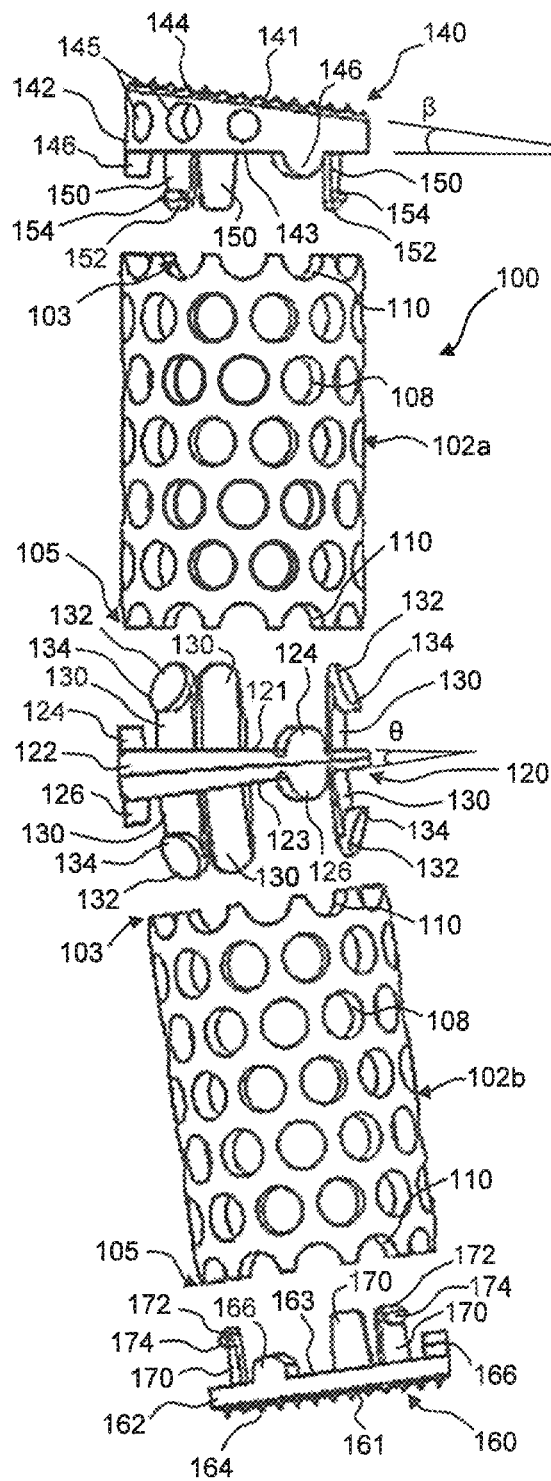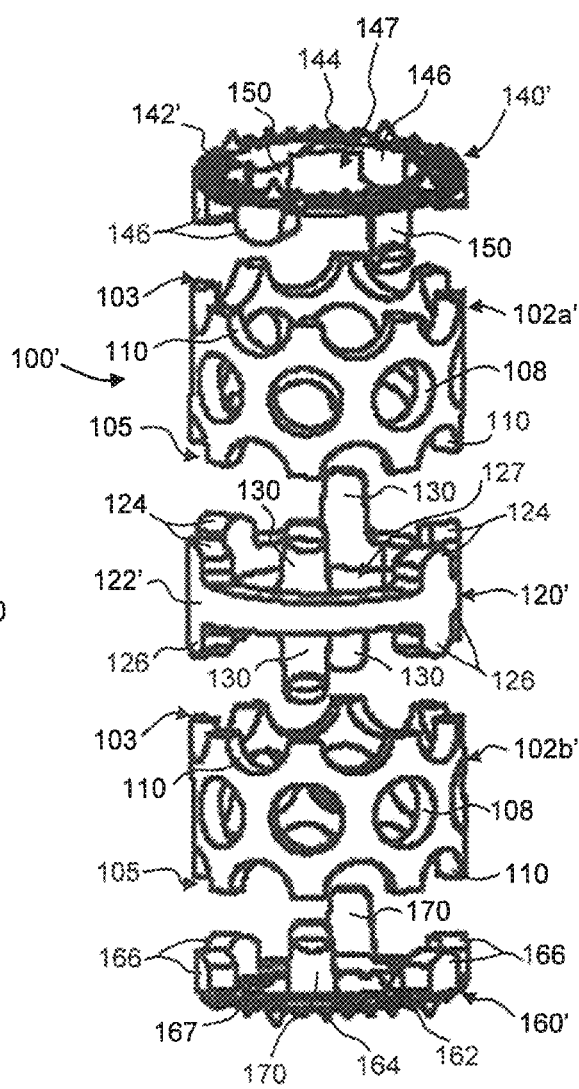
Fig. 6
Fig. 7

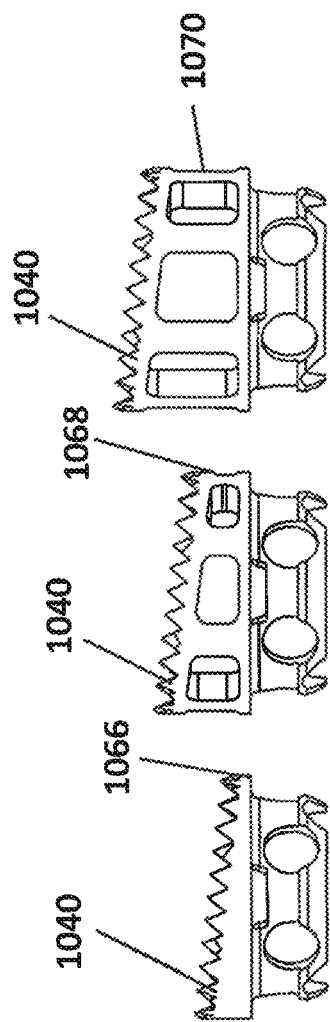

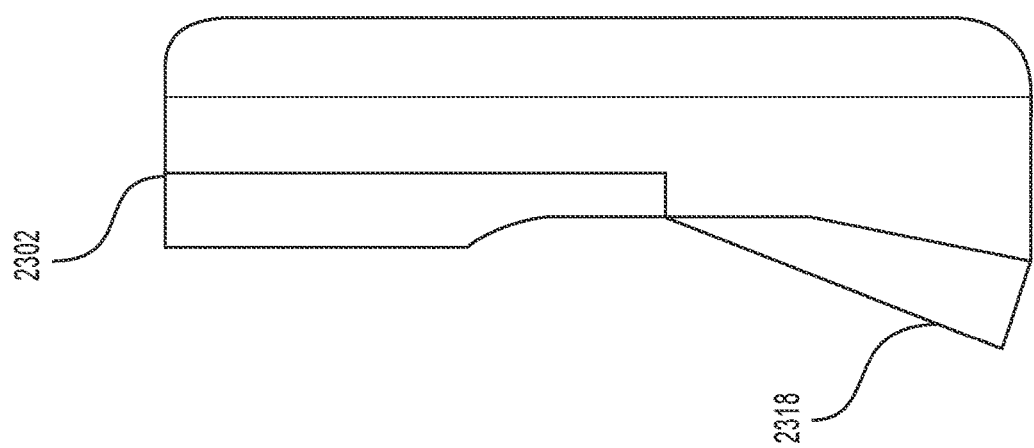

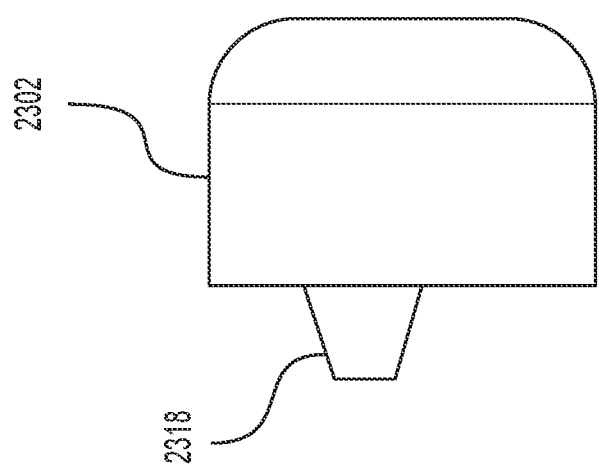

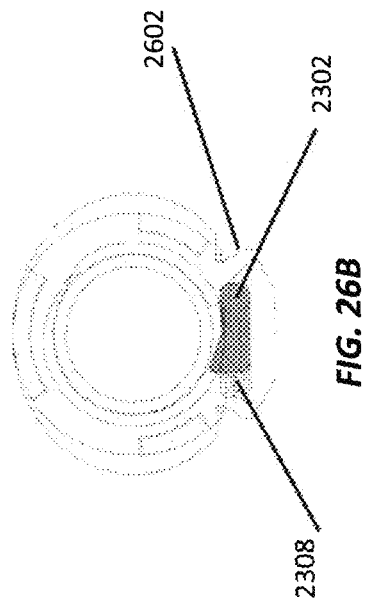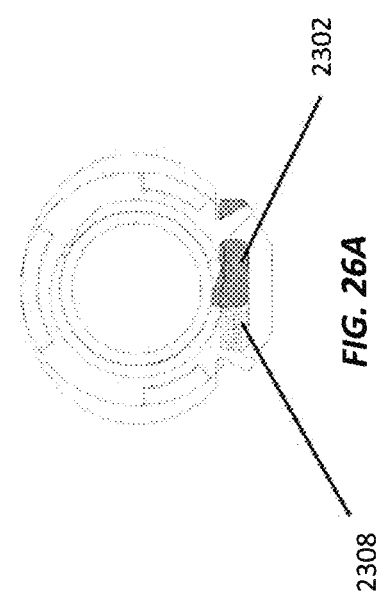

SYSTEMS AND METHODS FOR EXPANDABLE CORPECTOMY SPACER IMPLANTATION

CROSS-REFERENCE TO RELATED APPLICATION

This application is a continuation of U.S. patent application Ser. No. 17/094,177 filed on Nov. 10, 2020, which is a continuation-in-part of U.S. patent application Ser. No. 16/371,419 (published as U.S. Pat. Pub. 2019-0224023), which is a continuation of U.S. patent application Ser. No. 15/836,362, filed on Dec. 8, 2017 (now U.S. Pat. No. 10,278,834), which is a continuation-in-part application of U.S. patent application Ser. No. 15/264,974 filed on Sep. 14, 2016 (now U.S. Pat. No. 10,278,833), the contents of all of which are incorporated by reference herein in their entirety for all purposes.

FIELD

The present disclosure relates to systems and devices for supporting the spine after removal of at least a part of a vertebra. More particularly, the disclosure relates to vertebral body replacement implant assemblies and attachment assemblies.

BACKGROUND

Diseases and injury to bone structures, such as the vertebral column, and conditions requiring surgical intervention are relatively common. A variety of conventional implant or graft devices are presently available for use in specific areas. The devices vary in size, shape, materials used, and insertion techniques. For example, in the vertebral column, grafts may provide restoration, decompression, or stabilization of the spine. Typically, these devices include a member that is inserted in the vertebral column to replace an injured portion. An example of such a procedure is a corpectomy, which involves the replacement of all or a portion of the vertebral body with an implant or graft. One exemplary graft is a mesh corpectomy cage which is secured to the adjacent vertebrae via end plates to maintain the position of the implant in situ.

While these conventional devices may generally provide adequate results, they have several disadvantages. For example, often with a corpectomy that involves more than one level, the center segment of the corpectomy cage will settle into a position very close to the patient's dura and spinal cord due to the natural lordosis/kyphosis of the patient. Such proximity to the dura and spinal cord may cause pain, discomfort or further damage to the vertebral column.

Additionally, the endplates are typically secured to the cage with screws. The screws are often cumbersome to install and also make it more difficult to safely remove and replace any component of the construct. Furthermore, there is an inherent risk that the screws may be dropped during a procedure.

With respect to expandable vertebral body replacement (VBR) implants and cages, current expandable VBR cages have limited space for packing bone graft materials and are limited in allowing for bone graft material delivery into the implant after expansion. For example, an expansion range of the shortest expandable cage (15 mm) may only allow for 3-4 mm of expansion.

What is needed is an expandable mesh corpectomy spacer (which may also be used as an interbody spacer) that allows for bone graft material delivery after expansion and allows for up greater expansion for an implant with a starting height of 15 mm, for example.

SUMMARY

To meet this and other needs, a curved cage with press-fit endplates is provided. According to one embodiment, an implant assembly for engagement between a first vertebral body and a second vertebral body includes an inner core extending between a first end and a second end, a first outer core disposed on the first end, and a second outer core disposed on the second end. The inner core may be actuated in a first direction to move the first outer core and second outer core to an expanded configuration and the inner core may be actuated in a second direction to move the first outer core and the second outer core to a collapsed configuration.

According to another embodiment, an implant assembly for engagement between a first vertebral body and a second vertebral body includes an inner core extending between a first end and a second end, a first outer core disposed on the first end, a second outer core disposed on the second end, a first endplate configured to removably attach to the first outer core, and a second endplate configured to removably attach to the second outer core. The inner core may be actuated in a first direction to move the first outer core and second outer core to an expanded configuration and the inner core may be actuated in a second direction to move the first outer core and the second outer core to a collapsed configuration.

BRIEF DESCRIPTION OF THE DRAWINGS

The accompanying drawings, which are incorporated herein and constitute part of this specification, illustrate the presently preferred embodiments of the disclosure, and, together with the general description given above and the detailed description given below, serve to explain the features of the disclosure. In the drawings:

FIG. 6 is an exploded perspective view of the implant assembly of FIG. 1.

FIG. 7 is an exploded perspective view of another exemplary implant assembly.

FIGS. 12A-12C are perspective views of exemplary endcaps.

FIGS. 25A-D are perspective views of a locking mechanism for an expandable vertebral body replacement implant.

FIGS. 26A-B are top views of expandable vertebral replacement implant.

DETAILED DESCRIPTION

Figure 1:
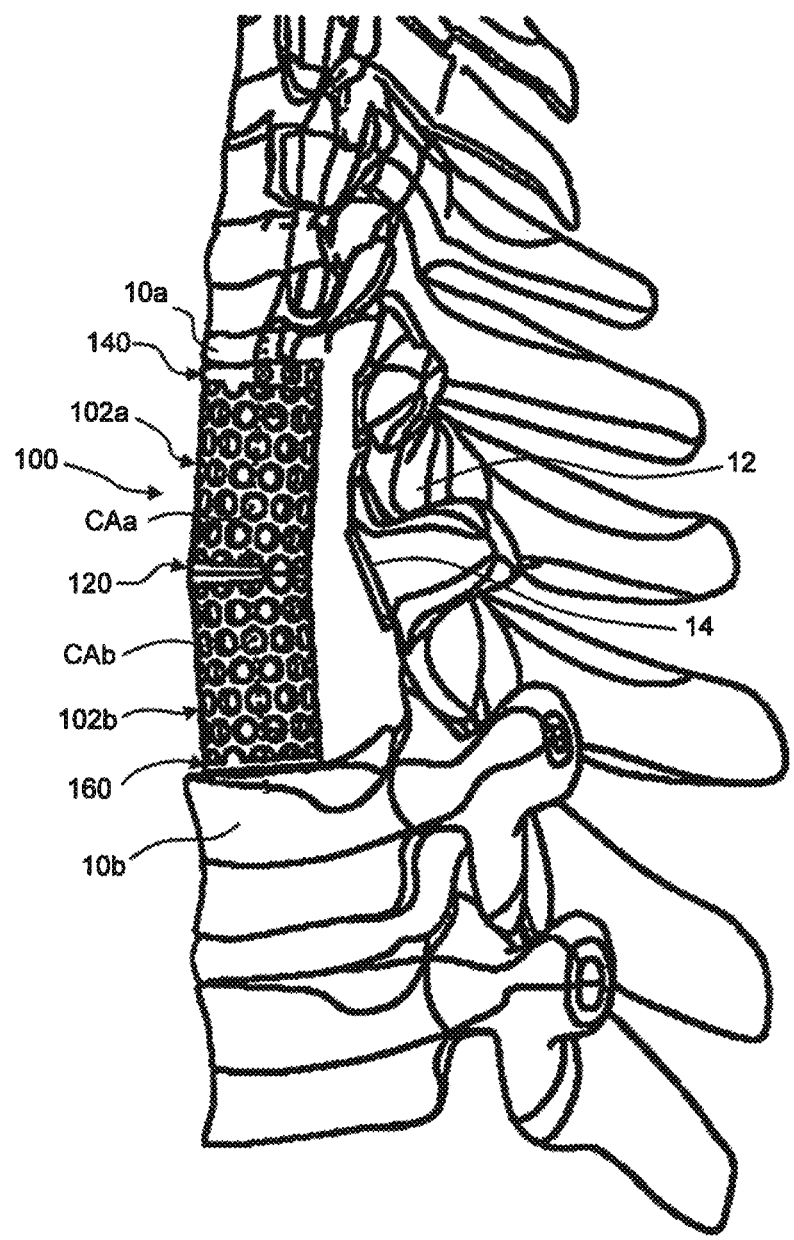
FIG. 1 is a side elevation view of an implant assembly according to an exemplary embodiment attached between vertebrae.

In the drawings, like numerals indicate like elements throughout, with alphabetical or prime identifiers indicating a particular one of the more generally identified element. Certain terminology is used herein for convenience only and is not to be taken as a limitation on the present invention. The following describes preferred embodiments of the present disclosure. However, it should be understood, based on this disclosure, that the invention is not limited by the preferred embodiments described herein.

Referring to FIG. 1, an exemplary implant assembly 100 in accordance with an embodiment of the disclosure is illustrated positioned between a pair of vertebrae 10a, 10b. The implant assembly 100 generally includes two or more mesh cages 102a, 102b, at least one intermediate plate 120 and a pair of endplates 140, 160. The intermediate plate 120 is secured between the cages 102a, 102b and has an angled configuration such that the central axis CAa of the cage 102a is angled at an acute angle α (see FIG. 9) relative to the central axis Cab of the cage 102b. The endplate 140 is secured to the end of cage 102a and secures the cage 102a to the adjacent vertebrae 10a. The endplate 160 is secured to the end of cage 102b and secures the cage 102b to the adjacent vertebrae 10b. The lordotic angle α created by the intermediate plate 120 helps to align the ends of the cages 102a, 102b with the vertebral endplates 10a, 10b which will help in minimizing subsidence. The lordotic angle α also positions the cages 102a, 102b away from the dura 14 and spinal cord 12 of the patient.

Figure 2:
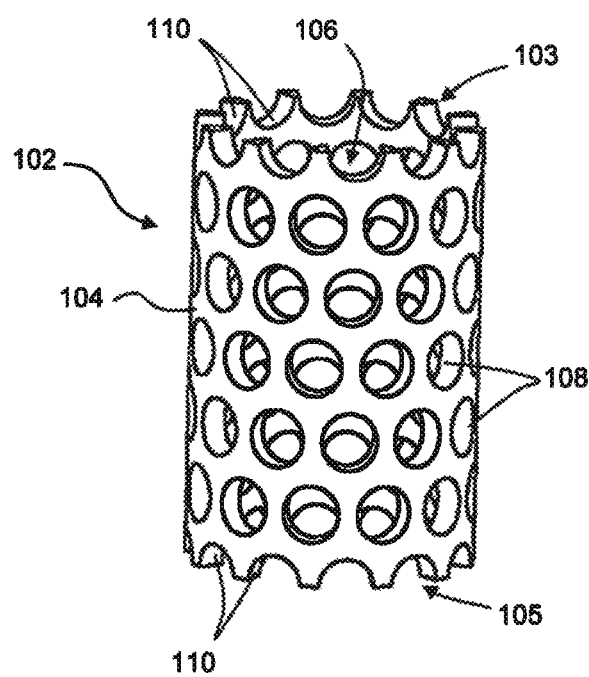
FIG. 2 is a perspective view of an exemplary cage member of the implant assembly of FIG. 1.
Figure 3:
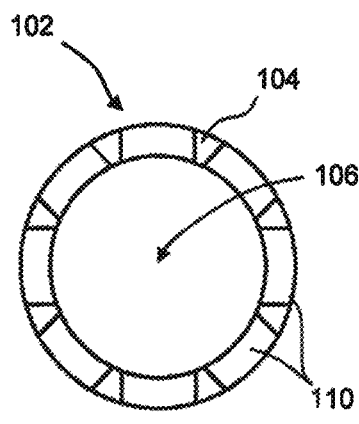
FIG. 3 is a top plan view of the cage member of FIG. 2.
Figure 4:
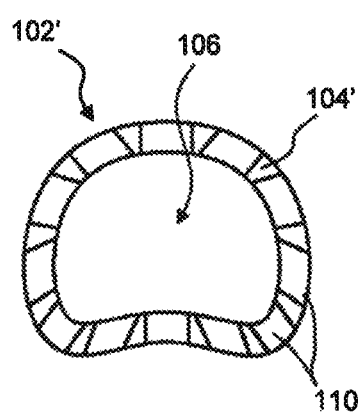
FIG. 4 is a top plan view of an alternative cage member.
Figure 5:
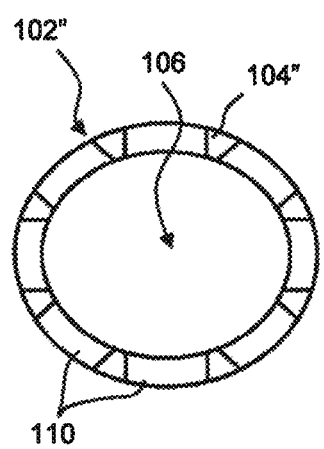
FIG. 5 is a top plan view of yet another alternative cage member.

Referring to FIGS. 2-5, exemplary embodiments of the cage 102 will be described. Each cage 102 generally has a hollow tubular body 104 extending between ends 103, 105 with a passage 106 therethrough. The tubular body 104 may be manufactured from various materials, for example, but not limited to, titanium or other metals, carbon fibers, ceramics, polymers or biocomposites. As illustrated in the embodiment of FIGS. 2 and 3, the exemplary cage 102 has a circular cross-section, however, the cage 102 may have various configurations. As two non-limiting examples, the cage 102' illustrated in FIG. 4 has a kidney shaped cross-section and the cage 102" illustrated in FIG. 5 has an oval cross-section. The mesh cages 102 may be supplied at various convenient lengths or can be cut to size. It is understood that the cages 102a, 102b of the implant assembly 100 may have the same or different lengths.

The tubular body 104 defines a series of radial openings 108 which open into the through passage 106. The radial openings 108 facilitate bone ingrowth and provide connection points for clips on the intermediate plate 120 and the endplates 140, 160, as will be described in more detail hereinafter. The openings 108 are preferably evenly spaced about the tubular body 104 to create a mesh thickness that offers compressive and torsional strength while allowing the cage to be easily cut to length. While the openings 108 are illustrated with a circular configuration, they openings 108 may have other shapes, for example, square or octagon.

Each end 103, 105 of the cage 102 includes a series of end openings 110 which open into the through passage 106 and are also open to the respective end surface of the tubular body 104. The end openings 110 are configured to receive tabs extending from the intermediate plate 120 and the endplates 140, 160 to provide rotational stability. While the end openings 110 are illustrated with a semi-circular configuration, they openings 108 may have other shapes, for example, square or octagon, and may have a depth that is more or less than one-half the width.

Exemplary intermediate plates 120, 120' and endplates 140, 140', 160, 160' will be described with reference to FIGS. 6-9. The differences between the components of the implant assembly 100 of FIG. 6 and the implant assembly 100' of FIGS. 7-9 will be identified, otherwise the components are substantially the same. With respect to the cages, the cages 102a' and 102b' are shorter than the cages 102a and 102b and have an oval configuration instead of the round configuration of the cages 102a and 102b.

Turning to the intermediate plates 120, 120', each plate 120, 120' has a ring shaped body 122, 122' with a passage 127 therethrough. The body 122 has a circular configuration to match that of the cages 102a, 102b while the body 122' has an oval configuration to match that of the cages 102a', 102b'. Each body 122, 122' extends between opposed contact surfaces 121, 123. The contact surfaces 121, 123 are at an angle θ relative to one another. This angle θ between the contact surfaces 121, 123 creates the lordotic angle α between the central axes CAa and Cab of the cages. In the event that more than two cages are utilized, intermediate plates 120 can be positioned between respective cages 102, each with the same or different angles θ.

On each body 122, 122', a plurality of tabs 124 extend from the contact surface 121 and a plurality of tabs 126 extend from the contact surface 123. The tabs 124, 126 have shapes which complement the shape of the end openings 110 such that the tabs 124, 126 are received in and engage the end openings 110 of the respective cages 102. Engagement between the tabs 124, 126 and the end openings 110 provides rotational stability between the intermediate plates 120, 120' and the cages 102. As seen in comparing the intermediate plate 120 with the intermediate plate 120', the number and location of tabs 124, 126 may be varied.

Additionally, the tabs 124, 126 may be eliminated provided the spring clips 130, described below, provide sufficient rotational stability.

A plurality of spring clips 130 extend from each contact surface 121, 123. As seen in comparing the intermediate plate 120 with the intermediate plate 120', the number and location of spring clips 130 may be varied. Each spring clip 130 includes a body 132 extending from the respective surface 121, 123 and defining a retaining ledge 134 spaced from the respective surface 121, 123. The bodies 132 may have different lengths to account for the angle between the contact surfaces 121, 123 such that each of the retaining ledges 134 on respective side of the intermediate plate 120, 120' are co-planar. With the retaining ledges 134 co-planar, the retaining ledges 134 will engage a common row of openings 108 in a respective cage 102 (see FIG. 9). Each spring clip body 132 is elastic such that it bends inward as spring clips 130 pass into the cage through passage 106, but then springs outward as the retaining ledge 134 aligns with a respective opening 108. The bodies 132 may have a tapered end surface to promote the inward bending of the spring clips 130 as they are inserted. The retaining ledges 134 thereby engage the openings 108 and axially secure the intermediate plate 120, 120' to the cages 102. If it is desired to remove the intermediate plate 120, 120' from the cages 102, the retaining ledges 134 are biased inward until they clear the openings 108 and the intermediate plate 120, 120' is easily disconnected.

Turning to the endplates 140, 140', each plate 140, 140' has a ring shaped body 142, 142' with a passage 147 therethrough. The body 142 has a circular configuration to match that of the cage 102a while the body 142' has an oval configuration to match that of the cage 102a'. Each body 142, 142' extends between opposed contact surfaces 141, 143, with the contact surface 141 being a bone contact surface and the contact surface 143 being a cage contact surface. The contact surfaces 141, 143 of the endplate 140 are at an angle β relative to one another while the contact surfaces 141, 143 of the endplate 140' are parallel to one another. The endplates 140, 140' can have an angled or parallel configuration. This angle θ, or lack of angle, between the contact surfaces 141, 143 allows the surgeon to make an implant assembly 100, 100' unique to the patient's anatomy.

On each body 142, 142', a plurality of projections 144 or the like extend from the contact surface 141 and are configured to engage the vertebrae contact surface. Various surface configurations may be utilized to achieve a desired securement with the vertebrae contact surface. Additionally, the body 142 may include radial openings 145 which promote bone growth into the endplate 140.

Similar to the intermediate plates, a plurality of tabs 146 extend from the contact surface 143. The tabs 146 have shapes which complement the shape of the end openings 110 such that the tabs 146 are received in and engage the end openings 110 of the respective cages 102. Engagement between the tabs 146 and the end openings 110 provides rotational stability between the endplates 140, 140' and the cages 102. As seen in comparing the endplate 140 with the endplate 140', the number and location of tabs 146 may be varied. Additionally, the tabs 146 may be eliminated provided the spring clips 150, described below, provide sufficient rotational stability.

A plurality of spring clips 150 extend from the contact surface 143. As seen in comparing the endplate 140 with the endplate 140', the number and location of spring clips 150 may be varied. Each spring clip 150 includes a body 152 extending from the surface 143 and defining a retaining ledge 154 spaced from the surface 143. With the endplate 140, the bodies 152 may have different lengths to account for the angle between the contact surfaces 141, 143 such that each of the retaining ledges 154 of the intermediate plate 140 are co-planar. With the endplate 140', the bodies 152 will have a common length such that the retaining ledges 154 are co-planar. With the retaining ledges 154 co-planar, the retaining ledges 154 will engage a common row of openings 108 in a respective cage 102 (see FIG. 9). Each spring clip body 152 is elastic such that it bends inward as spring clips 150 pass into the cage through passage 106, but then springs outward as the retaining ledge 154 aligns with a respective opening 108. The bodies 152 may have a tapered end surface to promote the inward bending of the spring clips 150 as they are inserted. The retaining ledges 154 thereby engage the openings 108 and axially secure the endplate 140, 140' to the cage 102. If it is desired to remove the endplate 140, 140' from the cage 102, the retaining ledges 154 are biased inward until they clear the openings 108 and the endplate 140, 140' is easily disconnected.

Turning to the endplates 160, 160', each plate 160, 160' has a ring shaped body 162, 162' with a passage 167 therethrough. The body 162 has a circular configuration to match that of the cage 102a while the body 162' has an oval configuration to match that of the cage 102a'. Each body 162, 162' extends between opposed contact surfaces 161, 163, with the contact surface 161 being a bone contact surface and the contact surface 163 being a cage contact surface. In the illustrated embodiments, the contact surfaces 161, 163 of each of the endplates 160, 160' are parallel to one another, however, it is understood that the surfaces 161, 163 may be angled relative to one another to allow the surgeon to make an implant assembly 100, 100' unique to the patient's anatomy.

On each body 162, 162', a plurality of projections 164 or the like extend from the contact surface 161 and are configured to engage the vertebrae contact surface. Various surface configurations may be utilized to achieve a desired securement with the vertebrae contact surface.

Similar to the intermediate plates, a plurality of tabs 166 extend from the contact surface 163. The tabs 166 have shapes which complement the shape of the end openings 110 such that the tabs 166 are received in and engage the end openings 110 of the respective cages 102. Engagement between the tabs 166 and the end openings 110 provides rotational stability between the endplates 160, 160' and the cages 102. As seen in comparing the endplate 160 with the endplate 160', the number and location of tabs 166 may be varied. Additionally, the tabs 166 may be eliminated provided the spring clips 170, described below, provide sufficient rotational stability.

A plurality of spring clips 170 extend from the contact surface 163. As seen in comparing the endplate 160 with the endplate 160', the number and location of spring clips 170 may be varied. Each spring clip 170 includes a body 172 extending from the surface 163 and defining a retaining ledge 174 spaced from the surface 163. With each of the endplates 160, 160', the bodies 172 will have a common length such that the retaining ledges 174 are co-planar. With the retaining ledges 174 co-planar, the retaining ledges 174 will engage a common row of openings 108 in a respective cage 102 (see FIG. 9). Each spring clip body 172 is elastic such that it bends inward as spring clips 170 pass into the cage through passage 106, but then springs outward as the retaining ledge 174 aligns with a respective opening 108. The bodies 172 may have a tapered end surface to promote the inward bending of the spring clips 170 as they are inserted. The retaining ledges 174 thereby engage the openings 108 and axially secure the endplate 160, 160' to the cage 102. If it is desired to remove the endplate 160, 160' from the cage 102, the retaining ledges 174 are biased inward until they clear the openings 108 and the endplate 160, 160' is easily disconnected.

Figure 8:
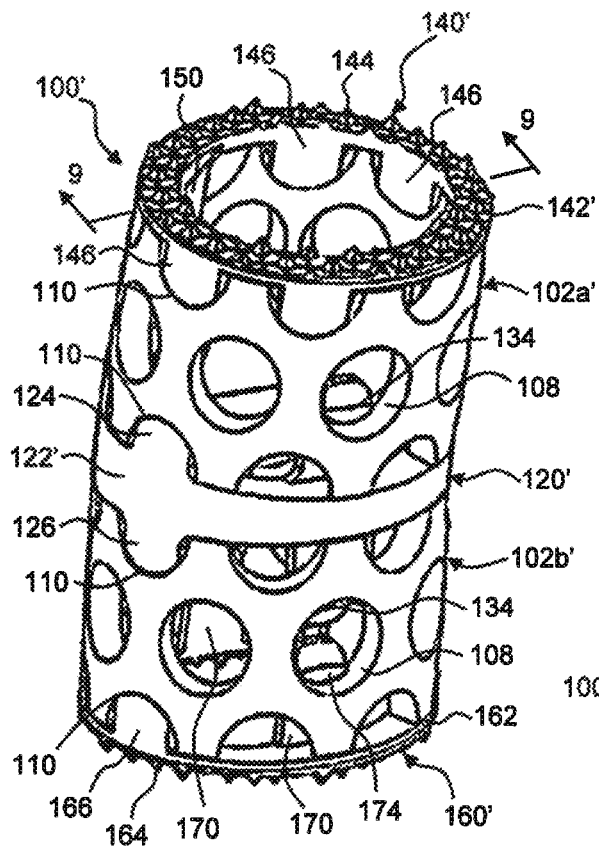
FIG. 8 is a perspective view of the implant assembly of FIG. 7 in an assembled configuration.
Figure 9:
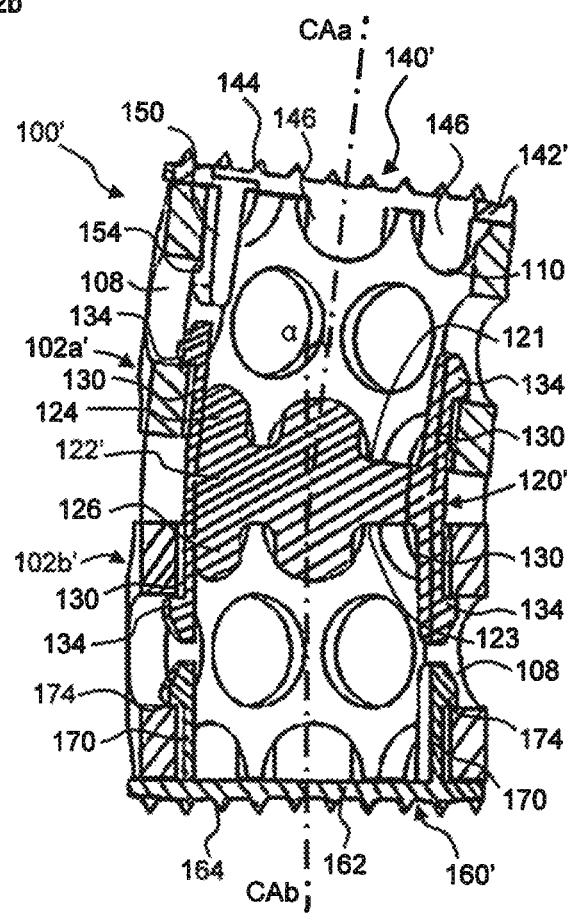
FIG. 9 is a cross-sectional view along the line 9-9 in FIG. 8.
Figure 10:
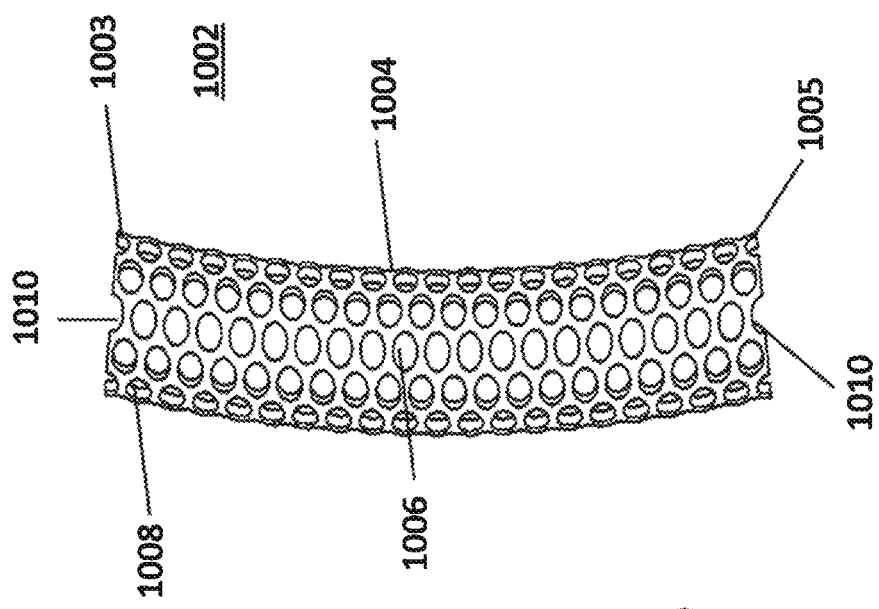
FIG. 10 is a perspective view of an exemplary cage member.

Upon assembly of the implant assemblies 100, 100', as illustrated in FIGS. 1 and 8-9, the integrated clips 130, 150, 170 on the intermediate plate and endplates snap into the corresponding holes 108 in the mesh cages 102 for a secure fit. The quick clip system makes a secure construct while allowing for components to be removed and replaced prior to insertion into the body should the need arise. The intermediate plate 120 offers a safe and secure connection to the mesh cages 102 while providing lordosis/kyphosis at the center of the construct instead of at the end of the cage only. This allows for the body of the implant assembly to be moved away from the dura and spinal cord of the patient.

Figure 15B:
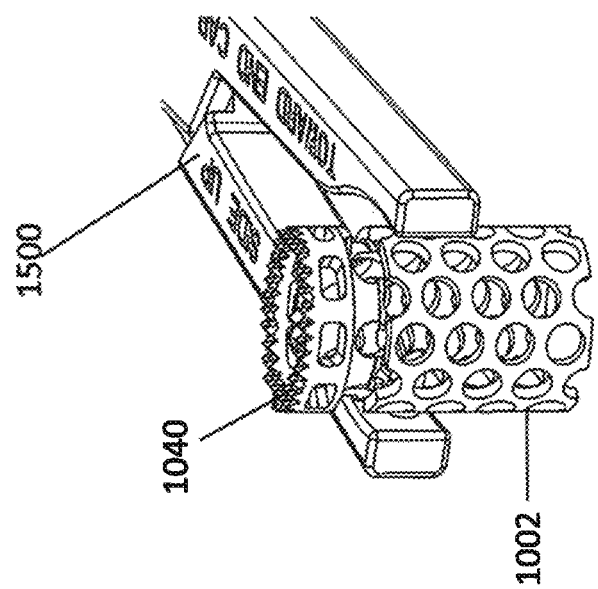
FIGS. 15A-15B are perspective views of an exemplary removal tool.
Figure 15A:
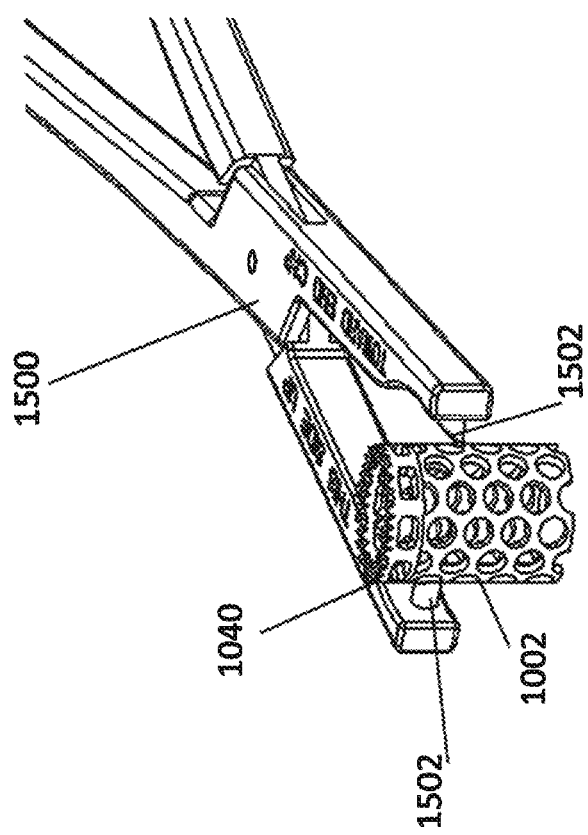

In a further embodiment, FIGS. 10-15B relate to components for an implant assembly 1000 (shown in FIGS. 15A-15B). Implant assembly 1000 is similar in structure to implant assembly 100 but does not contain, at least, the intermediate plates as discussed above. In FIGS. 10-15B, a cage 1002 generally has a hollow tubular body 1004 extending between ends 1003, 1005 with a passage 1006 therethrough. The tubular body 1004 may be manufactured from various materials, for example, but not limited to, titanium or other metals, carbon fibers, ceramics, polymers or biocomposites. Similar to the cage 102, cage 1002 may have a circular cross-section, a kidney shaped cross-section, or an oval cross-section as shown in FIGS. 2-5. The cage 1002 may be supplied at various convenient lengths or can be cut to size. Cage 1002 is illustrated as being curved so that a center section of cage 1002 may be positioned away from dura and spinal cord as previously discussed with respect to cage 102 shown in FIG. 1.

The tubular body 1004 may define a series of radial openings 1008 which open into the passage 1006. The radial openings 1008 may facilitate bone ingrowth and provide connection points for endplates 1040, 1060, as will be described in more detail hereinafter. The openings 1008 are preferably evenly spaced about the tubular body 1004 to create a mesh thickness that offers compressive and torsional strength while allowing the cage to be easily cut to length. While the openings 1008 are illustrated with a circular configuration, the openings 1080 may have other shapes, for example, square or octagon.

Each end 1003, 1005 of the cage 1002 includes at least one end opening 1010 which opens into the through passage 1006 and is also open to the respective end surface of the tubular body 1004. The end openings 1010 are configured to receive a tab 1064 extending from the endplates 1040, 1060 to provide rotational stability. While the end openings 1010 are illustrated with a semi-circular configuration, the openings 1010 may have other shapes, for example, square or octagon, and may have a depth that is more or less than one-half the width. Endplates 1040 and 1060 may be configured to have a tapered end 1062 that allows a tapered lead in point for the endplate 1040, 1060 when inserted into cage 1002. Endplates 1040 and 1060 are configured to press-fit or snap-fit into an end of cage 1002. A final fit may be achieved when an underside of an endplate is flush with an end of cage 1002 and tab 1064, which may be an anti-torsion tab, is seated in a partial hole, such as opening 1010.

The end caps may be angled with optional heights that a surgeon may use to make an implant assembly (e.g., implant assembly 1000) that is tailored to a specific patient's anatomy. Endcaps 1040 and 1060 may be accurately centered to each other and the cage 1002 by means of radial holes 1008 in cage 1002.

Figure 11A:
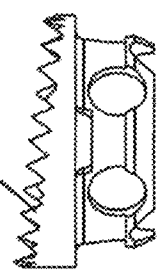
FIGS. 11A-11C are perspective views of exemplary endcaps.
Figure 11B:
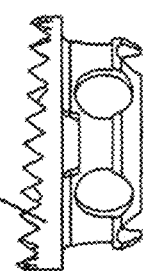
Figure 11C:
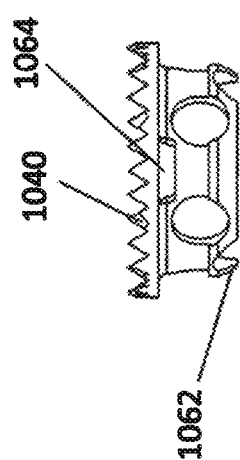

As shown in FIGS. 11A-12C, endcaps 1040 (and endcaps 1060) may have a variety of lordotic options that will allow a surgeon to choose an end cap that will closely match the lordosis of the patient. FIGS. 11A-C illustrate varying angles of endcap 1040. FIGS. 12A-C illustrate varying heights of endcap 1040. Further, each end cap 1040, 1060 may be available in a number of height options. For example, FIG. 12A may correspond to a height 1066 of 1.5 mm, FIG. 12B may correspond to a height 1068 of 3.5 mm, and FIG. 12C may correspond to a height 1068 of 5.5 mm. Varying height options may allow a surgeon to quickly remove and replace an end cap 1040 in the case when an implant assembly 1000 is too short or too long. An end cap removal tool 1500 may be supplied to facilitate the change. For example, as shown in FIGS. 15A-15B, removal tool 1500 may include opposing projections 1502 that are configured in a way to enter one of openings 1008 to engage tapered ends 1064 of the applicable endplate to remove the endplate out of cage 1002.

Figure 13B:
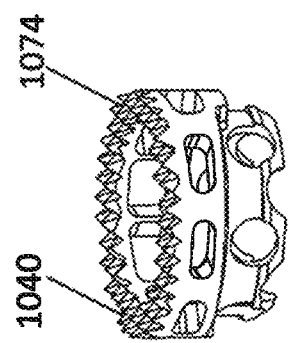
FIG. 13B is a perspective view of an exemplary endcap
Figure 13A:
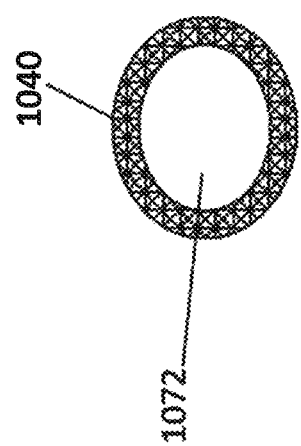
FIG. 13A is a top view of an exemplary endcap.
Figure 14B:
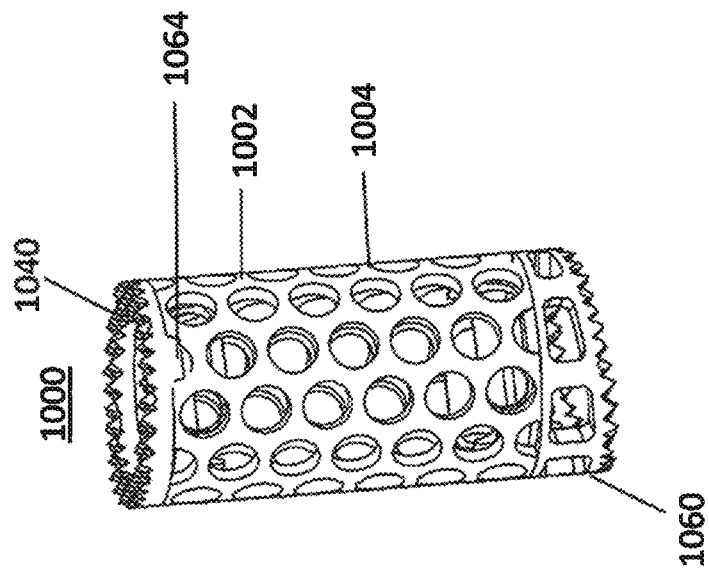
FIG. 14B is a perspective view of an exemplary implant assembly.
Figure 14A:
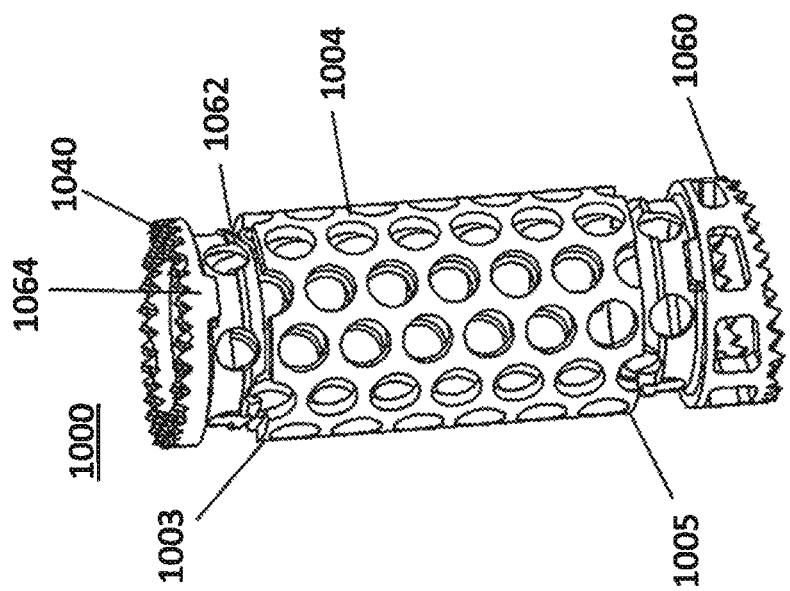
FIG. 14A is perspective view of an exemplary implant assembly prior to installation of exemplary endcaps.

As shown in FIGS. 13A-13B, an inner geometry 1072 of end cap 1040 may be free of mechanical protrusions, which may allow for a maximum graft window for insertion of bone growth material. A top surface of end cap 1040 may contain teeth 1074 (with or without a laser etched surface) that may aid implant assembly 1000 to grip a vertebral endplate and promote bony ingrowth.

Figure 16:
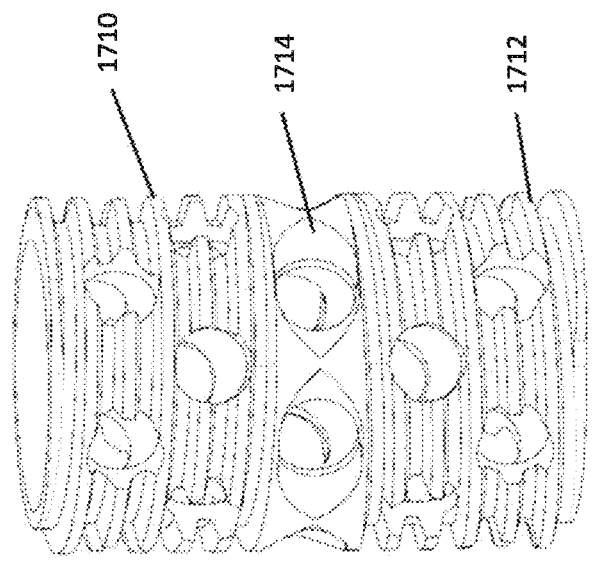
FIG. 16 is a perspective view of an exemplary inner core of an expandable vertebral body replacement implant.
Figure 17B:
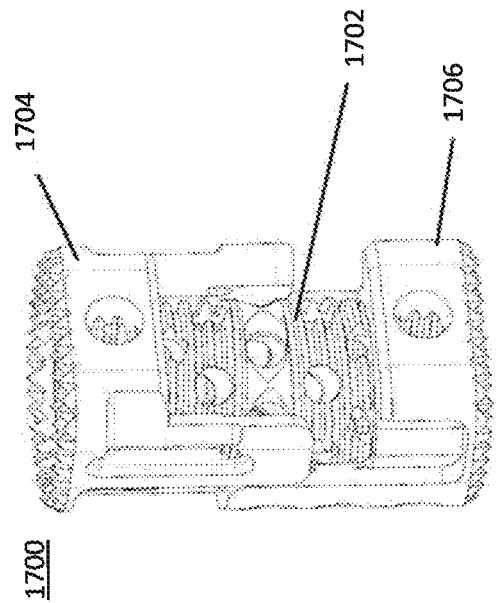
FIGS. 17A and 17B are perspective views of an expandable vertebral body replacement implant.
Figure 17A:
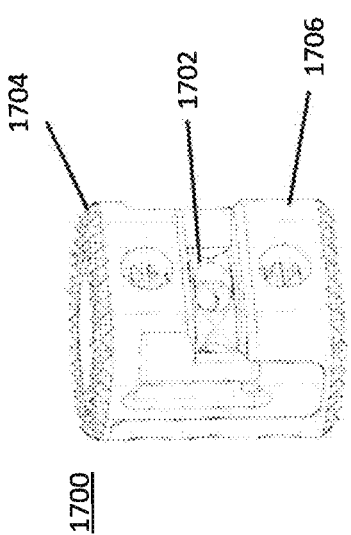
Figure 18:
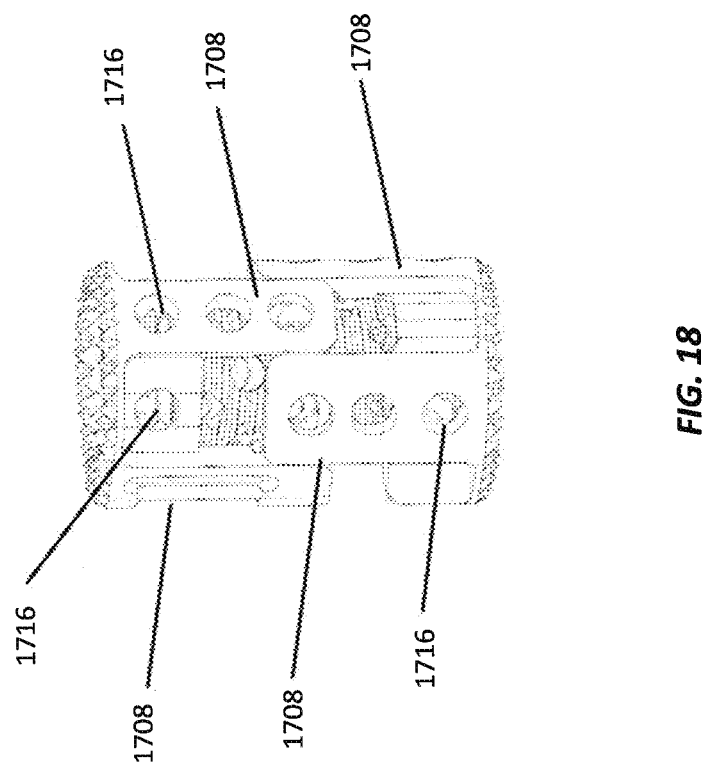
FIG. 18 is a perspective views of an expandable vertebral body replacement implant in an expanded configuration.

Referring now to FIGS. 16-18, an exemplary implant assembly 1700 in accordance with an embodiment of the disclosure is illustrated. Assembly 1700 is an expandable vertebral body replacement (VBR) implant. It may be used for corpectomies or as another type of interbody implant. Assembly 1700 may include three components. One component may be an inner core 1702 with a left-hand thread at one end and a right-hand thread at the opposite end. The other two components may be two outer cores 1704, 1706, one with left-hand internal threads and one with right-hand internal threads. Each outer core 1704, 1706 has mating rails 1708 (or fingers) that prevent torsional spin while allowing expansion, as illustrated in FIG. 18. Assembly 1700 may be locked into final position by a variety of mechanisms, including as described in greater detail with respect to FIGS. 23A-26.

An exemplary inner core 1702 is illustrated in FIG. 16. Inner core 1702 may have a left-handed thread at one end 1710 and a right-handed thread at the opposite end 1712. As inner core 1702 is turned in one direction by an inserter instrument via the set of center holes 1714, the implant 1700 expands as illustrated in FIGS. 17A and 17B. As an example, implant 1700 may allow for up to 8 mm of expansion for an implant with a starting height of 15 mm. Turned in the opposite direction, the implant contracts. The rails 1708 on outer cores 1704, 1706 mate to allow the outer cores 1704, 1706 to expand and prevent spin. Implant 1700 may be configured to be packed with bone graft material after expansion which may aid in fusion of the vertebral bodies through windows 1716.

Referring now to FIGS. 19A-22B, illustrated are exemplary embodiments of removable endplates 1902 for an expandable VBR assembly. By way of background, current VBR cages have endplates that attach to the end of the cage with screws. These screws may be easily dropped and add an extra step to expandable VBR assembly 1700 or 1900.

Figure 19C:
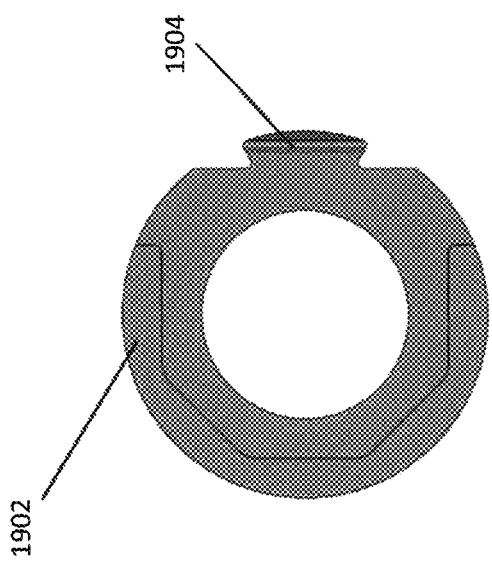
FIG. 19C is a top view of an expandable vertebral body replacement implant with an attached removable end plate.
Figure 19B:
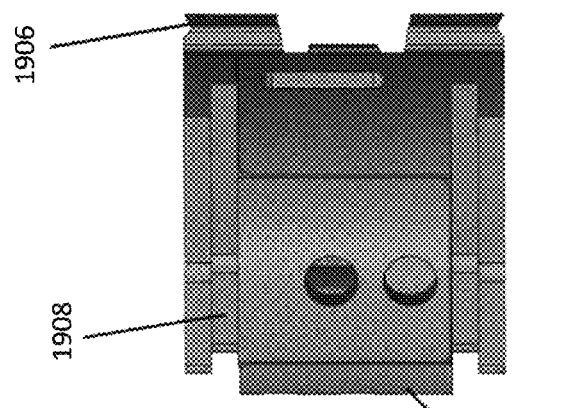
FIG. 19B is a perspective view of an expandable vertebral body replacement implant.
Figure 19A:
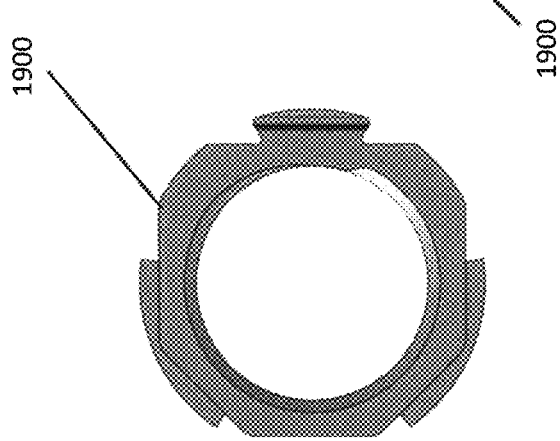
FIG. 19A is a top view of an expandable vertebral body replacement implant.

FIG. 19A illustrates an exemplary expandable VBR assembly 1900 from a top view and FIG. 19B illustrates assembly 1900 in a collapsed configuration from the side. FIG. 19C shows an underside of endplate 1902. Endplate 1902 may be an endplate that slides onto the end of the implant 1900 and configured to snap into place. The may be achieved by using a machined geometric relief 1904 on endplate 1902 and counter-relief 1906 on the implant assembly 1900. Endplate 1902 may slide into place with the use of a standard dado or undercut 1908. Undercut 1908 may be configured to prevent endplate 1902 from lifting off of assembly 1900.

Figure 20B:
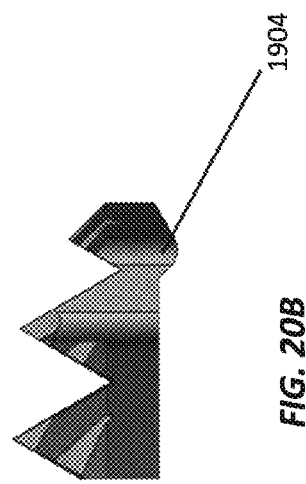
FIGS. 20A-20B are perspective views of an exemplary removable end plate for an expandable vertebral body replacement implant.
Figure 20A:
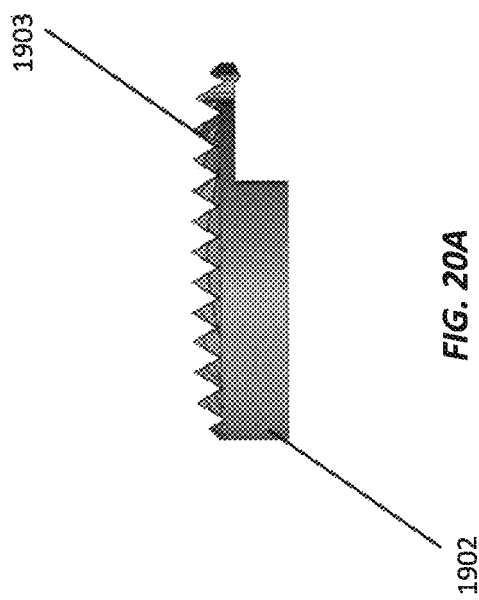
Figure 21:
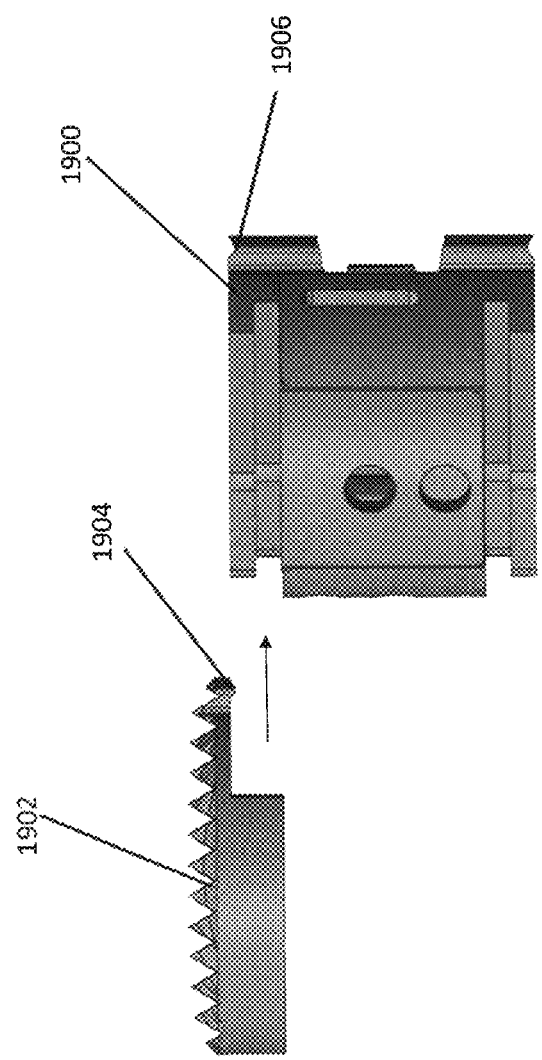
FIG. 21 is a perspective view of a removable endplate detached from an expandable vertebral body replacement implant.
Figure 22:
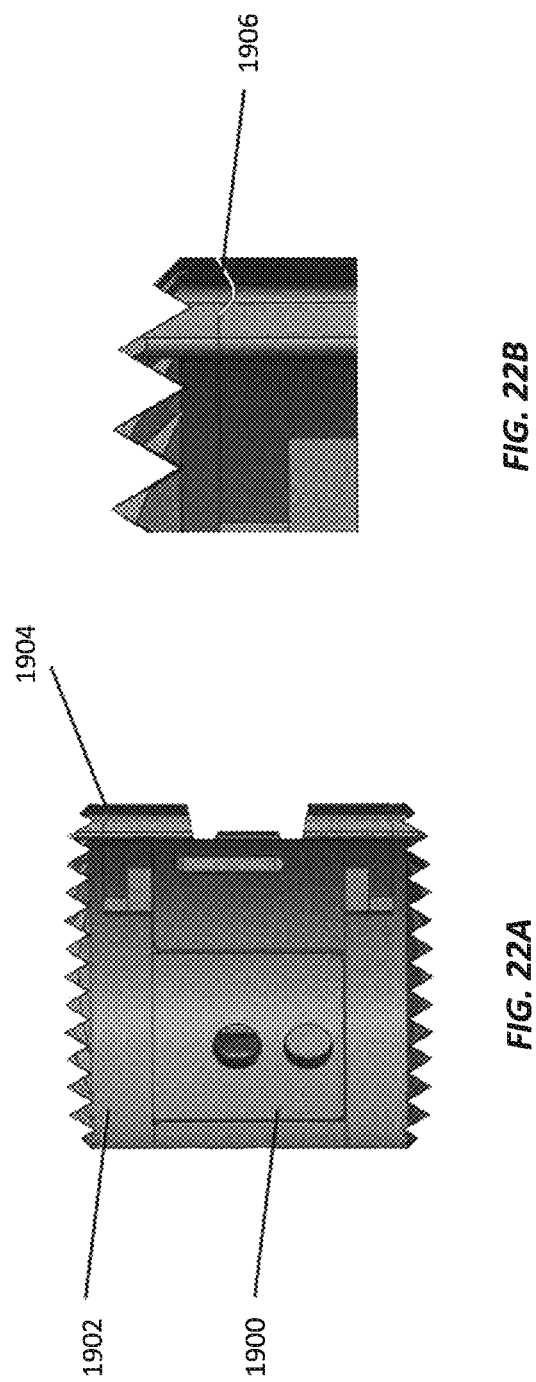
FIGS. 22A-22B are perspective view of a removable endplate attached to an expandable vertebral body replacement implant.
Figure 23:
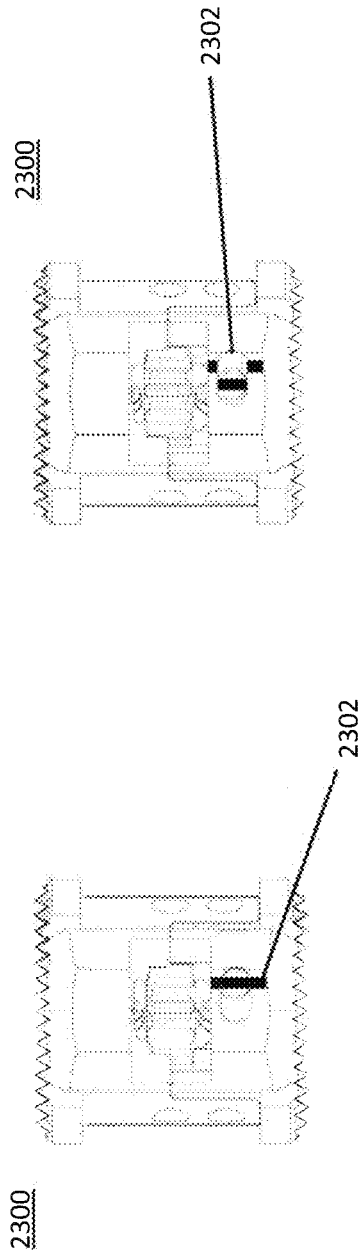
FIGS. 23A-B are perspective views of a an expandable vertebral replacement implant.

FIG. 20A illustrates a side view of endplate 1902 and FIG. 20B illustrates an expanded view of relief 1904 of endplate 1902. Endplate 1902 may have protrusions 1903 that may engage a vertebral body. As shown in FIG. 21, endplate 1902 is configured to attach to implant assembly 1900 by sliding on either end of assembly 1900. When fully attached, endplate 1902 snaps on the assembly 1900 as illustrated in FIG. 22A. FIG. 22B illustrates an expanded view of relief 1904 and counter-relief 1906 after attachment of endplate 1902. One advantage of the snap is that it eliminates the need for a separate screw to be used to hold endplate 1902 in place on the assembly 1900. It may also eliminates the need of an assembly block or fixture.

Referring now to FIGS. 23A-26B, an exemplary expandable VBR assembly 2300 consistent with the principles of the present disclosure is illustrated. Here, assembly 2300 includes a locking mechanism 2302. By way of background, expandable VBR cages need to be locked so as to prevent them from collapsing or losing height due to the natural vibration and/or movement of the human body into which they are implanted. Current implants available often use a locking screw that needs to be manually locked by the surgeon as a final step of the surgery. Due to the location in the body and approach of a corpectomy and the small size of the implant, the small size of the locking screw head and accessibility to it may prove to be difficult for the surgeon to locate, align and lock.

As shown in FIGS. 23A-26B, assembly 2300 may have locking mechanism 2302, which may be an automatic locking system for a surgical implant that securely locks the implant when the instrument that is used to insert the implant into the body is removed. This may eliminate the need to manually lock the implant as a final surgical step.

Assembly 2300 may have locking mechanism 2302 to automatically lock assembly 2300 in any position to prevent it from moving, winding down or collapsing from weight, external interference, movement or vibration. Locking mechanism may be seated within the interior portion of assembly 2300, with a visible gage to indicate that locking mechanism 2302 is locked or unlocked. The lock functions in conjunction with right-hand and left-hand threads as described earlier. The implant may contain one or two locks depending on size. For purpose of illustration, one lock is shown.

As shown in FIGS. 23A and 23B, when locking mechanism is engaged, an etched or engraved lines will be aligned to visually form a solid line as shown in FIG. 23A. In the unlocked position, the lines will appear separated or perpendicular to one another, as shown in FIG. 23B.

Figure 24:
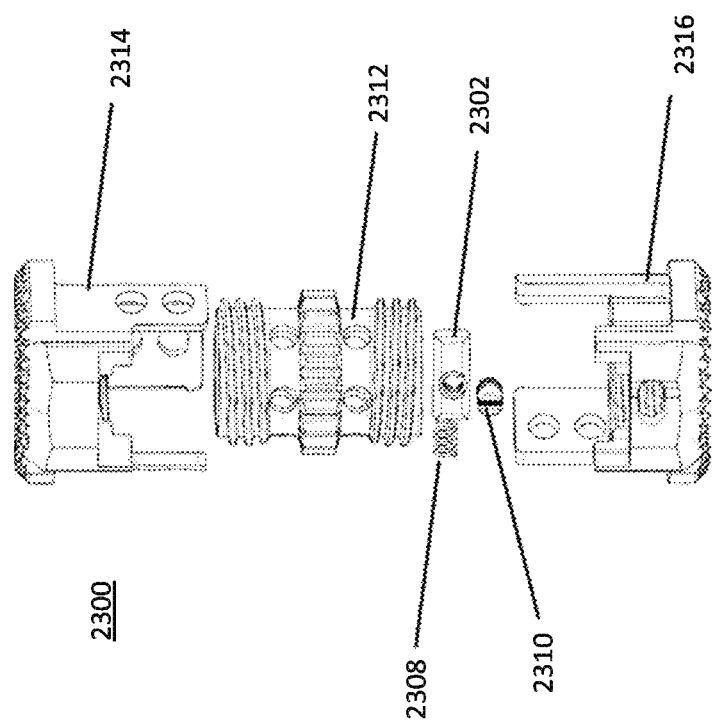
FIG. 24 is an exploded view of an expandable vertebral replacement implant.
Figure 25A:
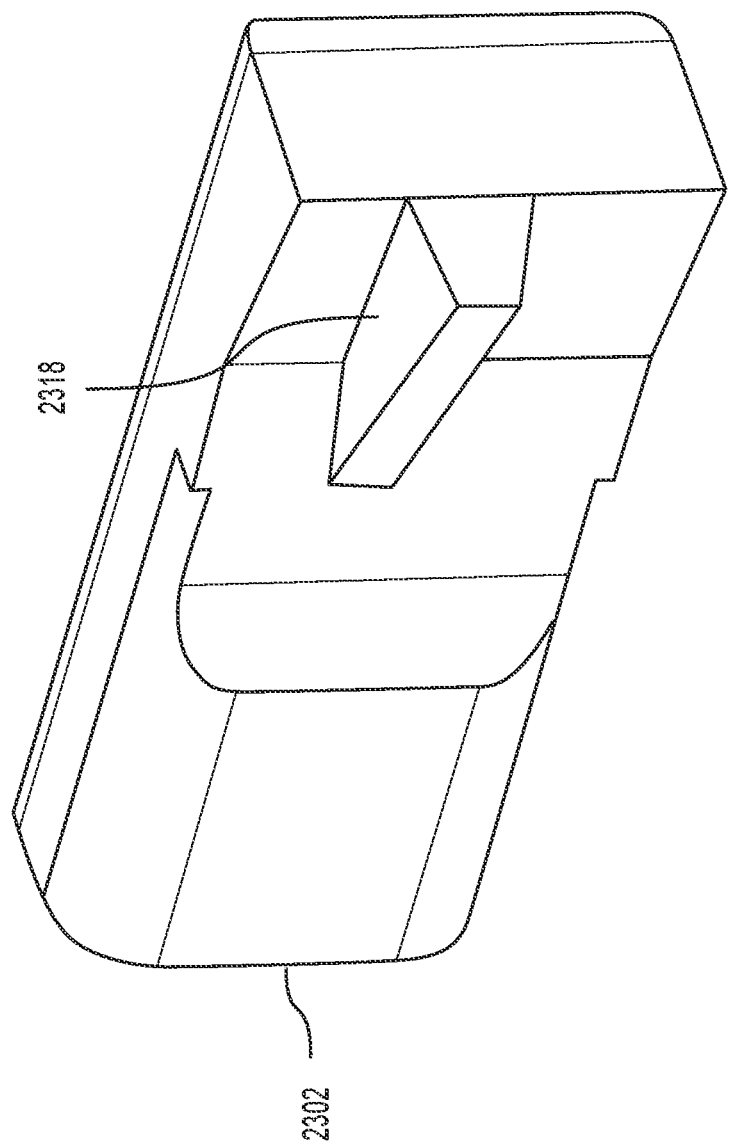
Figure 25C:
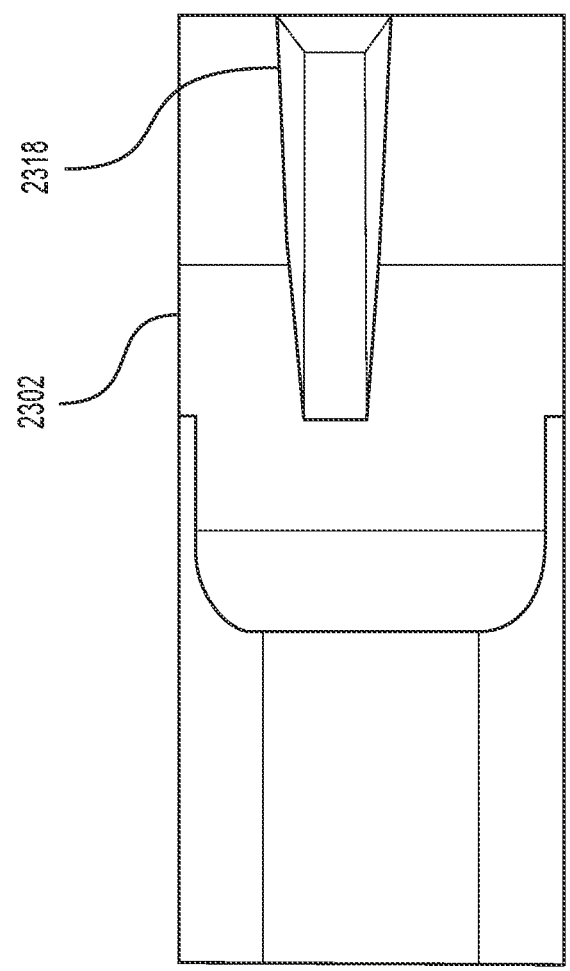

An exploded view of assembly 2300 is illustrated in FIG. 24. Assembly 2300 may include locking mechanism 2302, a spring mechanism 2308, a lock indicator 2310, inner core 2312 which may function as a threaded actuator as previously described, an outer core 2314 (right handed (RH) end), and an outer core 2316 (left handed (LH) end).

In practice, locking mechanism 2302 may be positioned inside of a cavity in outer core 2314 (RH end) or outer core 2316 (LH End) of assembly 2300. Spring mechanism 2308 assists by keeping constant tension on locking mechanism 2302 in the "locked" position. Spring mechanism 2308 is illustrated as a coiled compression spring. It may also take the form of a constant tension spring, a leaf spring, or any other form that exerts pressure against the locking mechanism 2302. Locking mechanism 2302 is disengaged into the un-locked position by a portion of the insertion instrument in the form of a wedge, clamp or screw, thereby allowing the implant to be expanded or contract by means of a drive gear. When the insertion instrument is removed from assembly 2300, locking mechanism 2302 is engaged as spring mechanism 2308 pushes locking mechanism 2302 into the locked position.

As illustrated in FIGS. 25A-25D, locking mechanism 2302 may be a tapered block tangent to the major diameter of the inner core 2312, with a centered tooth 2318, or multiple teeth, that are oversized to the minor diameter of inner core 2312. As locking mechanism 2302 is pushed into position, it wedges itself against the inner core 2312 and outer core 2314 (RH end) or outer core 2316 (LH end) to act as a "doorstop," preventing assembly 2300 from further movement.

FIG. 26A illustrates assembly 2300 in a locked position and FIG. 26B shows assembly 2300 in an unlocked position. At instrument insertion point 2602, an instrument pushes against locking mechanism 2302 to unlock assembly 2300 to expand or contract assembly 2300. One advantage of this configuration is that the locking of assembly 2300 occurs automatically once the insertion instrument is removed. The lock is not subject to surgical approach, visual alignment or physical access to a separate locking screw that may be difficult for the surgeon to see.

These and other advantages of the present disclosure will be apparent to those skilled in the art from the foregoing specification. Accordingly, it will be recognized by those skilled in the art that changes or modifications may be made to the above-described embodiments without departing from the broad inventive concepts. It should therefore be understood that this disclosure is not limited to the particular embodiments described herein, but is intended to include all changes and modifications that are within the scope and spirit of the disclosure as defined in the claims.

What is claimed is:

1. A method for stabilizing spinal elements comprising the steps of:
   providing an implant assembly for engagement between a first vertebral body and a second vertebral body comprising:
   an inner core extending between a first end and a second end;
   a first outer core disposed on the first end; and
   a second outer core disposed on the second end,
   wherein the inner core is configured to be actuated in a first direction to move the first outer core and second outer core to an expanded configuration and wherein the inner core is configured to be actuated in a second direction to move the first outer core and the second outer core to a collapsed configuration;
   wherein the first outer core and the second outer core contain one or more mating rails to prevent rotation of the first outer core and the second outer core during expansion; and
   positioning the implant assembly between the first vertebral body and the second vertebral body.

2. The method according to claim 1, wherein the first outer core is configured to engage the first vertebral body and the second outer core is configured to engage the second vertebral body.

3. The method according to claim 1, wherein the inner core includes left handed threading on the first end and right handed threading on the second end.

4. The method according to claim 1, wherein the inner core contains central holes configured to be engaged by an inserter instrument.

5. The method according to claim 1, wherein the first outer core and the second outer core contain one or more protrusions configured to engage one of the first vertebral body and the second vertebral body.

6. The method according to claim 1, wherein the first outer core and the second outer core are configured to receive a removable end plate.

7. The method according to claim 6, wherein the removable endplate contains a relief to engage a counter relief on one of the first outer core and the second outer core.

8. The method according to claim 1, further comprising a locking mechanism configured to lock the first outer core and the second outer core relative to the inner core.

9. The method according to claim 8, wherein the locking mechanism is configured to automatically lock the first outer core and the second outer core relative to the inner core via a spring mechanism.

10. A method for stabilizing spinal elements comprising the steps of:
providing an implant assembly for engagement between a first vertebral body and a second vertebral body comprising:
an inner core extending between a first end and a second end;
a first outer core disposed on the first end;
a second outer core disposed on the second end;
a first endplate configured to removably attach to the first outer core;
a second endplate configured to removably attach to the second outer core;
wherein the inner core is configured to be actuated in a first direction to move the first outer core and second outer core to an expanded configuration and wherein the inner core is configured to be actuated in a second direction to move the first outer core and the second outer core to a collapsed configuration;
wherein the first outer core and the second outer core contain one or more mating rails to prevent rotation of the first outer core and the second outer core during expansion; and
positioning the implant assembly between the first vertebral body and the second vertebral body.

11. The method according to claim 10, wherein the first endplate is configured to engage the first vertebral body and the second endplate is configured to engage the second vertebral body.

12. The method according to claim 10, wherein the inner core includes left handed threading on the first end and right handed threading on the second end.

13. The method according to claim 10, wherein the inner core contains central holes configured to be engaged by an inserter instrument.

14. The method according to claim 10, wherein the first endplate and the second endplate contain one or more protrusions configured to engage one of the first vertebral body and the second vertebral body.

15. The method according to claim 10, wherein the first outer core and the second outer core contain undercuts configured to engage one of the first endplate and the second endplate.

16. The method according to claim 10, wherein the first endplate and the second endplate contains a relief to engage a counter relief on one of the first outer core and the second outer core.

17. The method according to claim 10, further comprising a locking mechanism configured to lock the first outer core and the second outer core relative to the inner core.

18. The method according to claim 17, wherein the locking mechanism is configured to automatically lock the first outer core and the second outer core relative to the inner core via a spring mechanism.

* * * * *